(12) United States Patent
Justus et al.

(10) Patent No.: US 7,005,531 B2
(45) Date of Patent: Feb. 28, 2006

(54) METHOD OF MAKING IRON(III)GLUCONATE COMPLEX

(75) Inventors: Michael Justus, Schaffhausen (CH); Rolf Hänseler, Hallau (CH)

(73) Assignee: Cilag AG, Schaffhausen (CH)

( * ) Notice: Subject to any disclaimer, the term of this patent is extended or adjusted under 35 U.S.C. 154(b) by 0 days.

(21) Appl. No.: 10/991,748

(22) Filed: Nov. 18, 2004

(65) Prior Publication Data
US 2005/0256328 A1    Nov. 17, 2005

Related U.S. Application Data

(63) Continuation of application No. PCT/CH04/000299, filed on May 17, 2004.

(51) Int. Cl.
*C07F 15/02* (2006.01)
*A61K 31/295* (2006.01)

(52) U.S. Cl. ............. 556/146; 556/147; 514/502; 536/113

(58) Field of Classification Search ........... 556/146, 556/147; 514/502; 536/113
See application file for complete search history.

(56) References Cited

U.S. PATENT DOCUMENTS 6,693,211 B1    2/2004    Kumari et al. ............ 556/146
2003/0216566 A1 *  11/2003    Kumari et al. ............ 536/123.13
2005/0209322 A1 *   9/2005    Rangisetty et al. ......... 514/502

OTHER PUBLICATIONS

Folkert et al., American Journal of Kidney Diseases, vol. 41, No. 3, pp. 651-657 (Mar. 2003).*

* cited by examiner

*Primary Examiner*—Porfirio Nazario-Gonzalez
(74) *Attorney, Agent, or Firm*—Hoffmann & Baron, LLP

(57) ABSTRACT

The present invention refers to a method for making iron (III)gluconate complex, preferably alkali iron(III)gluconate complex. The method includes the following steps: (i) mixing a water soluble iron(III)salt in aqueous solution, simultaneously or in any desired sequence, with a member selected from gluconic acid, a water soluble salt of gluconic acid and combinations thereof, and a member selected from an alkali hydroxide, an alkali carbonate, an alkali hydrogen carbonate and combinations thereof, so that the reaction mixture has an acid value (pH-value) within the range of from 7.0 to 12, provided that when alkali hydroxide is used, gluconic acid or a water soluble salt of gluconic acid is provided at the beginning of the reaction or is added to the reaction mixture simultaneously with the alkali hydroxide; (ii) heating the reaction mixture until the iron(III)gluconate complex has formed; and (iii) adding an organic solvent which is miscible with water until the iron(III)gluconate complex is precipitated. The present invention also refers to pharmaceutical compositions including the iron(III)gluconate complex and methods of treating anemic conditions.

16 Claims, No Drawings

METHOD OF MAKING IRON(III)GLUCONATE COMPLEX

CROSS-REFERENCE TO RELATED APPLICATIONS

This application is a continuation of International Application No. PCT/CH04/000299, which designates the U.S., filed May 17, 2004, the contents of which are incorporated by reference herein.

FIELD OF THE INVENTION

The present invention refers to a method of making iron(III)gluconate complex, preferably of alkali iron(III) gluconate complex, especially sodium iron(III)gluconate complex.

BACKGROUND OF THE INVENTION

Alkali-iron gluconate complexes, especially sodium iron (III)gluconate complexes as well as methods of making these compounds are known. The sodium iron(III)gluconate complex contains organically bound iron and is being used as a therapeutic agent for increasing the iron content in the blood of humans and animals. In the following the term sodium iron(III)gluconate complex is used and it is understood herein that this term generally also comprises the alkali iron(III)gluconate complexes known.

U.S. Pat. No. 6,693,211 describes a method of making sodium iron(III)gluconate complex in sucrose by treating an aqueous solution of iron chloride with an aqueous solution of a selected weak alkali at about neutral acid value (pH). The formed chloride is then separated from the formed colloidal iron(III)oxyhydroxide and reacted with sodium gluconate at elevated temperature. The sodium iron(III) gluconate complex formed is then isolated and added to an aqueous solution of sucrose to yield sodium iron gluconate complex in sucrose.

The term "iron(III)gluconate complex" which is used in the following text also includes the alkali iron(III)gluconate complexes and the preferred sodium iron(III)gluconate complex.

The methods known have major disadvantages. One of the main problems present in all the methods for making iron(III)gluconate complex, e.g. sodium iron(III)gluconate complex, is the separation of the chloride content resulting from the iron chloride, especially the separation of the counter ion formed from the iron oxyhydroxide. This content of anions is physiologically undesirable. In known methods this chloride content is separated from the slushy iron(III)oxyhydroxide. However, it is known that it is very difficult to filter freshly precipitated colloidal iron oxyhydroxide. Aged iron oxyhydroxide is easy to filter, but it cannot be used for the syntheses of physiologically active sodium iron(III)gluconate complex. Therefore the iron oxyhydroxide is being sloshed several times whereby the remaining solution is decanted. This method is technically impractical and expensive.

For producing solid sodium iron(III)gluconate complex, made as described herein before, the complex is being freeze-dried. This process generally is complicated because the chloride must be separated entirely before freeze-drying. Freeze-drying itself is a time consuming procedure consuming a lot of energy.

The method according to the present invention does not have these disadvantages. It is for example not necessary to separate the chloride content from the freshly precipitated colloidal iron oxyhydroxide. It is further possible to obtain the solid iron(III)gluconate complex by simple precipitation, for example by using an organic solvent, so that the sodium iron(III)gluconate complex made according to the present invention does not contain any undesired carrier materials or additives. Handling iron(III)gluconate complexes as a solid material is considerably easier and safer than handling a corresponding solution, as the solid material has a much smaller volume and may be transported over long distances without decomposition. The danger of introducing microbiologic impurities is very small for solid materials. It is further much easier to purify solid materials and to separate side product therefrom in comparison to purifying solutions. Therefore, it is a distinct advantage to precipitate the pure product without the addition of any auxiliary compounds.

For the production of the sodium iron(III)gluconate complex in sucrose, the sodium iron(III)gluconate complex made according to the present invention is simply added to the sucrose solution; no heating is required for the formation of the sodium iron(III)gluconate/sucrose complex. After sterile filtration a preparation is obtained which is suitable for the parenteral iron therapy. For sterilizing the solution it is also possible to heat the solution using e.g. vapor sterilization. The sucrose within the sucrose solution is, according to the present invention, no integral part of the active compound but an auxiliary compound of the formulation only. It can be shown, e.g. with gel-permeation chromatography, that the sucrose can be separated completely from the injection solution containing the sodium iron(III)gluconate complex made according to the present invention, without causing any physical change of the sodium iron(III)gluconate complex. According to the present invention, the desired active compound is already entirely formed in solution before precipitation and is precipitated without any change. This further simplifies considerably the subsequent preparation of the injection solution.

SUMMARY OF THE INVENTION

The method of the present invention is defined in the claims. The present invention especially refers to a method of making iron(III)gluconate complex, preferably alkali iron(III)gluconate complex, preferably sodium iron(III)gluconate complex, including the following steps:

(i) mixing a water soluble iron(III)salt, preferably iron (III)chloride hexahydrate, in aqueous solution, simultaneously or in any desired sequence, with gluconic acid or a water soluble salt of gluconic acid, preferably alkali-D-gluconate, preferably sodium-D-gluconate, and an alkali hydroxide and/or alkali carbonate and/or alkali hydrogen carbonate, preferably at a low temperature, so that the reaction mixture has an acid value (pH-value) within the range of from 7.0 to 12, preferably a weak basic pH-value within the range of 7.5<pH<10.5; whereby when alkali hydroxide is used: always gluconic acid or a water soluble salt of gluconic acid is provided at the beginning of the reaction or is added to the reaction mixture simultaneously with the alkali hydroxide; and (ii) heating the reaction mixture until the iron(III)gluconate complex has formed entirely, preferably at a temperature within the range of from 70° C. to reflux temperature; and adding a suitable organic solvent which is miscible with water, preferably methanol, ethanol and/or acetone, preferably ethanol, until the iron(III)gluconate complex is precipitated, whereby the iron(III)gluconate complex is purified from the anions present, preferably chloride anions, before or after precipitation, using any known method.

The present invention also refers to iron(III)gluconate complexes produced according to the present invention, preferably alkali iron(III)gluconate complex, especially sodium iron(III)gluconate complex, as well as the use of these compounds for the production of pharmaceuticals, preferably for the treatment of anemic conditions. The present invention further refers to pharmaceuticals, which contain the iron(III)gluconate complex made according to the present invention.

DETAILED DESCRIPTION OF THE INVENTION

According to the present invention it is possible to react the water soluble iron(III)salt directly with gluconic acid or a salt of gluconic acid, preferably sodium-D-gluconate, to obtain iron(III)gluconate complex, preferably sodium iron (III)gluconate complex, whereby the reaction is carried out in a weak alkaline aqueous medium, for example by using sodium hydroxide, whereby for the reaction preferably gluconic acid or a salt of gluconic acid is initially provided. It is assumed that within the reaction in situ iron(III)oxyhydroxide is formed. As a preferred embodiment the iron(III) oxyhydroxide, which is formed in the weak alkaline aqueous medium, is not isolated, but is in situ directly reacted with gluconic acid, preferably sodium gluconate, whereby the corresponding iron(III)gluconate complex, preferably sodium iron(III)gluconate complex, is formed. The colloidal dissolved complex can optionally be pre-purified e.g. be dialyzed, ultra filtered, or be pre-purified by using ion exchange, precipitation of salts, i.e. of the salts produced within the reaction, for example from an excess of sodium hydrogen carbonate, from a concentrated solution or by using another known filtration technique. As mentioned above, also other water-soluble salts can be used in place of iron(III)chloride hexahydrate, however, the use of iron(III) chloride hexahydrate has the advantage of being cheap and easy to handle. Examples of such water-soluble iron(III)salts are iron(III)nitrate hexahydrate or iron(III)nitrate nonahydrate.

The iron(III)gluconate complex, which optionally has been pre-purified, can be purified entirely from chloride ions after precipitation in a simple manner. However, it is a critical feature of the invention that it suffices to purify the final iron(III)gluconate complex only from any chloride ions present, which is considerably simpler than the precipitation or sloshing of the humid iron(III)oxyhydroxide. It is surprising that according to the present invention also alkali hydroxide can be used.

Preferably iron(III)chloride hexahydrate is reacted with at least 0.1 equivalent (per equivalent iron(III)chloride hexahydrate), preferably with 0.1–5.0 equivalent, preferably with 0.1–2.0 equivalent, preferably with about 0.2–0.5 equivalent, sodium-D-gluconate. The reaction is carried out preferably at low temperatures, i.e. at a temperature within the range of from −10° C. to 50° C., preferably at about 5° C. to 25° C., in a solution containing enough base, preferably alkali hydroxide such as sodium hydroxide, lithium hydroxide, potassium hydroxide, ammonium hydroxide or mixtures thereof, preferably sodium hydroxide, so that a weak basic pH-value is obtained, i.e. a pH-value from about 7 to about 12, preferably a pH from 7.5<pH<10.5, preferably a pH from 7.7<pH<9.7, preferably a pH from 8<pH<9.5. The addition of about 2.5 to 5.0 equivalent of base, preferably about 3 equivalent, preferably alkali hydroxide (per equivalent iron(III)chloride hexahydrate) generally suffices. The mixture is then heated to a temperature of at least about 70° C., preferably to reflux temperature. It is also possible to work at elevated pressure and heat to a temperature up to 140° C. whereby the solid material which may have precipitated dissolves. In order to obtain the desired form of the product (with respect to molecular weight, pH-value, color) the mixture is heated to reflux temperature for at least 0.2 hours, preferably for 0.5–96 hours, preferably for about 1–5 hours. It is also possible to work at elevated pressure and heat to a temperature up to 140° C. The complex formed is then purified, optionally without previous separation, with known methods such as filtration, ultra filtration, ion exchange or dialysis or any other known method. The mixture is then concentrated and methanol, ethanol and/or acetone or another suitable water-soluble organic solvent is added until the active compound is precipitated. The product can subsequently be isolated, for example by filtration or centrifugation.

It is advantageous to pre-purify the formed iron(III) gluconate complex from chloride anions directly after its formation, optionally after cooling and concentrating the reaction mixture. If the product is not pre-purified, the obtained product is preferably precipitated and further purified, e.g. precipitated or sloshed, from a solvent/water mixture (within the weight ratio of 1:1–5:1) for reaching the required chloride specification. The complex does not change during concentration and precipitation. The complex isolated is identical with the complex obtained in solution after heating.

A further embodiment of the present invention is that iron(III)chloride hexahydrate is dissolved in water, preferably at a temperature within the range of from −10° C. to about 40° C., preferably about 5° C. to 25° C. An aqueous solution is then added containing about 1.5–5.0 equivalent, preferably about 1.5–2.0 equivalent, of alkali carbonate, such as sodium carbonate, lithium carbonate, potassium carbonate, ammonium carbonate, or mixtures thereof, preferably sodium carbonate, or an aqueous solution containing about 3.0–10.0 equivalent, preferably about 3.0–4.0 equivalent alkali hydrogen carbonate such as sodium bicarbonate, potassium bicarbonate, lithium bicarbonate, ammonium bicarbonate or mixtures thereof, preferably sodium bicarbonate, where upon iron(III)oxyhydroxide precipitates. The iron(III)oxyhydroxide is reacted, either without isolation in situ or optionally after isolation, with at least 0.1 equivalent, preferably with 0.1–5.0 equivalent, preferably with about 0.2–1.0 equivalent, preferably with about 0.5 equivalent, of gluconic acid or an alkali salt thereof, preferably sodium-D-gluconate. The reaction mixture is then heated, preferably to a temperature of at least 70° C. and preferably to reflux temperature. It is also possible to work under pressure and to heat up to about 140° C. The complex formed is then preferably purified, optionally after previous separation from the reaction mixture. Purification may be carried out using conventional methods such as filtration, ultra filtration, ion exchange or dialysis or any other known method. The mixture is then concentrated so that it remains well flowable and further treated as described above for other embodiments of the invention.

In this sense the present invention also refers to a process for the preparation of sodium ferric gluconate complex in sucrose, comprising the steps of:
 a) combining ferric chloride salt solution with alkaline earth metal and ammonium salts chosen from the group consisting of sodium carbonate, sodium bicarbonate, lithium carbonate, potassium carbonate, potassium bicarbonate, ammonium carbonate, ammonium bicarbonate and mixtures there of; to form the ferric oxyhydroxide;

b) combining ferric oxyhydroxide and sodium gluconate in solution to yield the sodium ferric gluconate complex; and c) combining sodium ferric gluconate with sucrose in solution to yield the desired sodium ferric gluconate complex in sucrose. Preferred is the process in which the ferric chloride salt is ferric chloride hexahydrate. Preferred is the process in which the alkaline earth metal salt is sodium carbonate.

The following examples for making the sodium iron(III) gluconate complexes illustrate the present invention.

EXAMPLE 1

45.73 g (169.2 mmol) iron(III)chloride hexahydrate and 7.40 g (33.9 mmol) sodium-D-gluconate are dissolved in 500 ml water at room temperature. To the clear solution there are added at room temperature 50.0 ml (498 mmol) of sodium hydroxide (30% by weight concentration). A slightly brown suspension is obtained. The mixture is then heated to reflux temperature for one hour whereby a clear nearly black solution is formed. The product is precipitated by adding 3.0 liter of acetone while stirring and slowly cooling to 20–40° C. The brown suspension formed is stirred over night, filtered at room temperature and washed with acetone. The wet product is cleaned by sloshing twice with a mixture of 600 ml acetone and 200 ml water. The product is then dried at 50° C. under vacuum. 15.25 g of a brown powder is obtained which can be used according to analytical results (i.a. gel permeation-chromatography) for the treatment of parenteral iron therapy.

EXAMPLE 2

135.6 g (501.7 mmol) iron(III)chloride hexahydrate and 21.86 g (100.2 mmol) sodium-D-gluconate are dissolved at room temperature in 1600 ml water. 150.0 ml (1490 mmol) of sodium hydroxide (30% by weight) is added at room temperature to the clear solution. A slightly brown suspension is formed. The reaction mixture is then heated to reflux for one hour whereby a clear nearly black solution is obtained. The mixture is dialyzed over night. The solution is concentrated to about 15% of the original volume and precipitated by adding 600 ml acetone. The brown suspension formed is stirred for one hour, filtered, and washed with acetone. The product is dried at 50° C. under vacuum. 36.73 g of a brown powder is obtained which can be used, according to analytical results (i.a. gel permeation-chromatography), for the treatment of parenteral iron therapy.

EXAMPLE 3

27.58 g (102.0 mmol) iron(III)chloride hexahydrate are dissolved at room temperature in 200 ml water. 440 ml of a 7.5% (by weight) solution of sodium hydrogen carbonate in water (409 mmol) are slowly added, to avoid strong foaming of the solution. After addition of about half of the solution a flaky solid starts to precipitate. After addition of the entire base the suspension is further stirred until the formation of gas is terminated. 4.53 g (20.77 mmol) sodium-D-gluconate is added. The reaction mixture is then heated for one hour to reflux temperature. A clear nearly black solution is obtained. The solution is concentrated to 25% of the original volume. Precipitation is obtained by the addition of 200 ml methanol while cooling slowly to 20–40° C. The brown suspension obtained is stirred for 30 minutes at room temperature, filtered, and washed with methanol. The wet product is dissolved in 33.0 g water and precipitated 50 ml methanol. The solid material is filtered and washed with methanol. The product is dried at 50° C. under vacuum. 10.32 g of a brown powder is obtained, which according to analysis (i.a. gel permeation-chromatography) is suitable for the use in parenteral iron therapy.

EXAMPLE 4

13.68 g (50.6 mmol) iron(III)chloride hexahydrate are dissolved in 100 ml water at room temperature in water. 215.0 ml of a 7.5% (by weight) solution of sodium hydrogen carbonate in water (200 mmol) are slowly added at room temperature, so that the solution does not foam too much. After addition of about half of the solution a flaky precipitate starts to form. After addition of the base is completed the suspension is further stirred until the formation of gas is terminated. 2.26 g (10.4 mmol) sodium-D-gluconate is added to the suspension and the reaction mixture is heated for one hour to reflux temperature. A clear nearly black solution is obtained which is concentrated to 35% of the original volume. Precipitation is obtained by the addition of 100 ml acetone and slowly cooling to 20–40° C. The brown suspension obtained is stirred for 30 minutes at room temperature, filtered, and washed with methanol. The wet product is purified by sloshed twice with a mixture of 60 ml acetone and 60 ml water. The product is dried at 50° C. under vacuum. 8.88 g of a brown powder is obtained which according to analysis (i.a. gel permeation-chromatography) is suitable for the use in parenteral iron therapy.

EXAMPLE 5

140.55 g (520 mmol) iron(III)chloride hexahydrate are dissolved in 400 ml water at room temperature. 225.12 g (786.8 mmol) sodium carbonate decahydrate dissolved in 590 ml water are added slowly at room temperature to avoid strong foaming. After addition of about two thirds of the solution a flaky solid starts to precipitate. After the addition of the base has been completed the suspension formed is further stirred until the formation of gas has stopped. 22.40 g (102.7 mmol) sodium-D-gluconate is then added to the suspension. The mixture is then heated for one hour to reflux temperature. A clear nearly black solution is obtained. The mixture is filled into a dialysis pipe and dialyzed over night under slight flow of water. Precipitation of the product is obtained by addition of 1000 ml methanol and slow cooling to 20–40° C. The brown suspension is stirred for 30 minutes at room temperature, filtered, and washed with methanol. 63.21 g of a brown powder is obtained which according to analysis (i.a. gel permeation-chromatography) is suitable for the use in parenteral iron therapy.

EXAMPLE 6

13.70 g (50.7 mmol) iron(III)chloride hexahydrate are dissolved in 100 ml water at room temperature. A solution of 16.97 g (201.7 mmol) sodium carbonate in 209.2 g water is added within a temperature range of 10–25° C., so that the solution does not foam too strongly. After addition of about half of the solution a flaky solid starts to precipitate. After the addition of the base has been completed the suspension obtained is further stirred until the formation of gas has stopped. The precipitate is filtered and washed with water. 5.51 g (25.3 mmol) sodium-D-gluconate and 55.9 g pure water are added to the wet product and heated for one hour to reflux temperature. A clear nearly black solution is obtained. The mixture is concentrated to 20% of its original volume and precipitated by the addition of 39.6 g methanol and slowly cooling to 20–40° C. The brown suspension obtained is stirred for 30 minutes at room temperature, filtered and washed with methanol. The product is dried at 50° C. under vacuum. 8.94 g of a brown powder is obtained which according to analysis (i.a. gel permeation-chromatography) is suitable for the use in parenteral iron therapy.

EXAMPLE 7

54.06 g (200 mmol) iron(III)chloride hexahydrate are dissolved in 79.5 g water at room temperature. 31.8 g (300 mmol) sodium carbonate dissolved in 147 ml water is added at room temperature, so that the solution does not foam too much. When most of the solution has been added a flaky precipitate is obtained. After the entire base has been added the suspension obtained is further stirred until the formation of gas has stopped. 21.81 g (100 mmol) sodium-D-gluconate is added to the suspension. The mixture is then heated during three hours to reflux temperature. A clear nearly dark solution is obtained. The mixture is filled into dialysis pipes and dialyzed over night under slight flow of water. 17.49 g (80.2 mmol) sodium-D-gluconate is added. The mixture is dropped into 500 ml methanol and slowly cooled to 20–40° C. whereby the product precipitates. The brown suspension is stirred for 30 minutes at room temperature, filtered, and washed with methanol. 42.13 g of a brown powder is obtained which according to analysis (i.a. gel permeation-chromatography) is suitable for the use in parenteral iron therapy.

What is claimed is:

1. Method of making alkali iron(III)gluconate complex, comprising the following steps:
   (i) mixing a water soluble iron(III)salt in aqueous solution, simultaneously or in any desired sequence, with a member selected from the group consisting of gluconic acid, a water soluble salt of gluconic acid and combinations thereof, and a member selected from the group consisting of an alkali hydroxide, an alkali carbonate, an alkali hydrogen carbonate and combinations thereof, so that the reaction mixture has an acid value (pH-value) within the range of from 7.0 to 12, provided that when alkali hydroxide is used, gluconic acid or a water soluble salt of gluconic acid is provided at the beginning of the reaction or is added to the reaction mixture simultaneously with the alkali hydroxide;
   (ii) heating the reaction mixture until the alkali iron(III) gluconate complex has formed; and
   (iii) adding an organic solvent which is miscible with water until the alkali iron(III)gluconate complex is precipitated.

2. Method according to claim 1, wherein the alkali iron(III)gluconate complex is purified from anions present, before or after precipitation.

3. Method according to claim 1, wherein the alkali iron(III)gluconate complex is a sodium iron(III)gluconate complex.

4. Method according to claim 1, wherein the water-soluble iron(III)salt is iron(III)chloride hexahydrate.

5. Method according to claim 1, wherein the salt of gluconic acid is alkali-D-gluconate.

6. Method according to claim 5, wherein the alkali-D-gluconate is sodium-D-gluconate.

7. Method according to claim 1, wherein the reaction in step (i) is carried out at a pH-value within the range of 7.5<pH<10.5, and the reaction mixture in step (ii) is heated to a temperature within the range of 70° C. to reflux temperature for at least 0.2 hours.

8. Method according to claim 1, wherein the alkali iron(III)gluconate complex formed is precipitated by the addition of a member selected from the group consisting of methanol, ethanol, acetone and combinations thereof.

9. Method according to claim 1, wherein alkali hydroxide is added and the water soluble iron(III)salt is directly reacted with gluconic acid or a salt of gluconic acid to yield the alkali iron(III)gluconate complex.

10. Method according to claim 2, wherein the purification is a method selected from the group consisting of dialysis, ultra filtration, ion exchange and precipitation of salts.

11. Method according to claim 1, further comprising refluxing at elevated pressure.

12. Method according to claim 11, wherein the refluxing is conducted for about 1 to about 5 hours at temperatures up to 140° C.

13. Method according to claim 1, wherein in step (i) there is provided iron(III)chloride hexahydrate together with at least 0.1 equivalent (per equivalent iron(III)chloride hexahydrate) sodium-D-gluconate, at a temperature within the range of −10° C. to 50° C.; and
   adding thereto a solution containing an alkali hydroxide selected from the group consisting of sodium hydroxide, lithium hydroxide, potassium hydroxide, ammonium hydroxide and mixtures thereof, until a pH of about 7 to about 12 is reached.

14. Method according to claim 1, wherein in step (i) iron(III)chloride hexahydrate is dissolved in water and, at a temperature within the range of from −10° C. to about 40° C., an aqueous solution containing about 1.5–5.0 equivalent alkali carbonate selected from the group consisting of sodium carbonate, lithium carbonate, potassium carbonate, ammonium carbonate and mixtures thereof, or an aqueous solution containing about 3.0–10.0 equivalent alkali hydrogen carbonate selected from the group consisting of sodium bicarbonate, potassium bicarbonate, lithium bicarbonate, ammonium bicarbonate and mixtures thereof, is added, whereby iron(III)oxyhydroxide is precipitated; and
   said iron(III)oxyhydroxide is reacted, without isolation in situ or after previous isolation, with at least 0.1 equivalent gluconic acid or an alkali salt thereof, and heating the reaction mixture to at least 70° C.

15. Method according to claim 14, wherein an aqueous solution of 1.5–2.0 equivalent alkali carbonate or an aqueous solution of 3.0–4.0 equivalent alkali hydrogen carbonate is added to an aqueous solution of iron(III)chloride hexahydrate, at a temperature within the range of 5° C. to 25° C.; and
   reacting the iron(III)oxyhydroxide without isolation in situ or after isolation with 0.1–5.0 equivalent gluconic acid or an alkali salt thereof.

16. Method according to claim 1, wherein the alkali iron(III)gluconate complex is purified or pre-purified by a method selected from the group consisting of filtration, ultra filtration, ion exchange and dialysis; and
   concentrating the reaction mixture to remain well flowable and further treating the mixture.

* * * * *